US 8,161,972 B2

(12) United States Patent
Isaza

(10) Patent No.: US 8,161,972 B2
(45) Date of Patent: *Apr. 24, 2012

(54) DETECTING VENTILATOR SYSTEM ANOMALIES WHILE IN A SPEAKING MODE

(75) Inventor: Fernando Isaza, Carlsbad, CA (US)

(73) Assignee: RIC Investments, LLC, Wilmington, DE (US)

( * ) Notice: Subject to any disclaimer, the term of this patent is extended or adjusted under 35 U.S.C. 154(b) by 1263 days.

This patent is subject to a terminal disclaimer.

(21) Appl. No.: 11/893,796

(22) Filed: Aug. 17, 2007

(65) Prior Publication Data

US 2008/0060656 A1 Mar. 13, 2008

Related U.S. Application Data

(63) Continuation-in-part of application No. 11/518,816, filed on Sep. 11, 2006, now Pat. No. 7,997,272.

(51) Int. Cl.
*A61M 16/00* (2006.01)
*F16K 31/02* (2006.01)
*A62B 9/02* (2006.01)

(52) U.S. Cl. ......... 128/207.16; 128/207.14; 128/204.18; 128/204.21; 128/205.24

(58) Field of Classification Search ............. 128/204.21, 128/204.18, 205.24, 207.14, 207.15, 207.16
See application file for complete search history.

(56) References Cited

U.S. PATENT DOCUMENTS

| | | | |
|---|---|---|---|
| 4,219,020 A | 8/1980 | Czajka | |
| 4,280,492 A * | 7/1981 | Latham | 128/207.15 |
| 4,538,607 A * | 9/1985 | Saul | 128/207.16 |
| 4,759,356 A | 7/1988 | Muir | |
| 5,813,399 A | 9/1998 | Isaza et al. | |
| 6,189,534 B1 * | 2/2001 | Zowtiak et al. | 128/207.16 |
| 6,230,708 B1 | 5/2001 | Radko | |
| 6,401,713 B1 * | 6/2002 | Hill et al. | 128/204.21 |
| 6,543,449 B1 | 4/2003 | Woodring et al. | |
| 6,626,175 B2 | 9/2003 | Jafari et al. | |
| 6,668,824 B1 | 12/2003 | Isaza et al. | |
| 6,823,866 B2 | 11/2004 | Jafari et al. | |
| 7,156,090 B2 * | 1/2007 | Nomori | 128/200.26 |
| 7,617,824 B2 * | 11/2009 | Doyle | 128/204.21 |
| RE41,345 E * | 5/2010 | Blom | 128/207.14 |

* cited by examiner

*Primary Examiner* — Justine Yu
*Assistant Examiner* — Rachel Young

(57) ABSTRACT

A method of operating a ventilator assembly having inhalation and exhalation passages communicating with one another, and a respiration assembly that can perform repetitive respiratory cycles. The method includes (a) repetitively cycling the respiration assembly so that during the inhalation phase, gas in the inhalation passage flows to the patient, and during the exhalation phase, an exhalation valve is maintained relatively closed and the exhaled gases flow pass the vocal cords and out of the mouth thereby facilitating the patient's ability to speak, (c) monitoring the pressure within at least one of the passages during the exhalation phase, and (d) determining whether a circuit disconnect or an occlusion exists based on the pressure monitoring.

28 Claims, 11 Drawing Sheets

DETECTING VENTILATOR SYSTEM ANOMALIES WHILE IN A SPEAKING MODE

CROSS-REFERENCE TO RELATED APPLICATIONS

This application is a Continuation-in-Part (CIP) of, and claims priority under 35 U.S.C. §120 from, U.S. patent application Ser. No. 11/518,816, filed Sep. 11, 2006, the contents of which are incorporated herein by reference.

BACKGROUND OF THE INVENTION

1. Field of the Invention

This application relates to ventilation of a patient, and, more particularly, to a method and apparatus for invasive ventilation that allows the patient to speak while being ventilated and that detect system anomalies when the ventilator is operating in a speaking mode.

2. Description of Related Art

An example of a known endotracheal tube assembly is disclosed in U.S. Pat. No. 4,759,356 ("the '356 patent"), the entire disclosure of which is hereby incorporated by reference into the present specification. An example of a known ventilator assembly is disclosed in U.S. Pat. No. 6,543,449 ("the '449 patent"), the entire disclosure of which is hereby incorporated by reference into the present specification.

The endotracheal tube assembly disclosed in the '356 patent includes an endotracheal tube configured to be installed into a patient's trachea so that an inner open end communicates with the patient's airway and lungs and an outer open end is suitably anchored exteriorly of the patient's neck. The '356 patent discloses the provision of a check valve on the open end of the tube, often referred to in the art as a "talking valve." The check valve disclosed in the '356 patent is in widespread use and the '356 patent specification indicates many advantages of the check valve when in use in addition to the basic talking advantage function.

The ventilator assembly disclosed in the '449 patent has the capability of invasive use, as with an endotracheal tube assembly, or non-invasive use, as with a mask. The present invention focuses on the invasive mode of ventilator operation.

As stated in the '356 patent, there are many advantages in addition to the talking capability which result from the use of a check valve. However, there are disadvantages as well. For example, the check valve should be removed in order to give the patient aerosol treatments or to perform suctioning.

U.S. Pat. No. 6,668,824 ("the '824 patent) teaches detecting tubing circuit disconnection and occlusions. The algorithm used in the '824 patent to detect circuit disconnections and occlusions requires detecting the exhalation gas flow during the exhalation phase of a breath, i.e., detecting the flow of gas traveling through the expiratory limb of the patient circuit during exhalation. The exhalation flow, in combination with at least one other monitored parameter, such as exhalation pressure, is used to detect circuit disconnections and occlusions. This technique, however, cannot be used if the ventilation mode implemented by the ventilator specifically avoids or does not require a flow of gas in the expiratory limb during exhalation.

SUMMARY OF THE INVENTION

Accordingly, it is an object of the present invention to provide a method of operating a ventilator assembly in a speaking mode that allows the patient to speak while receiving the ventilation therapy and that monitors for anomalies to maximize the safety of the ventilator while in the speaking mode. This object is achieved according to one embodiment of the present invention by (a) providing a ventilator assembly that includes inhalation and exhalation passages communicating with one another, and a respiration assembly capable of performing repetitive respiratory cycles. Each respiratory cycle includes: (1) an inhalation phase during which (i) an inhalation valve communicating with the inhalation passage is relatively open for the passage of gas therethrough into the inhalation passage and to patient, and (ii) an exhalation valve between the exhalation passage and an exhalation outlet in the ventilator assembly is relatively closed, and (2) an exhalation phase during which the inhalation valve is relatively closed. The method further includes (b) repetitively cycling the respiration assembly so that (1) during the inhalation phase, the gas in the inhalation passage flows through an endotracheal tube and into the patient's airway and lungs below the patient's vocal cords, and (2) during the exhalation phase, the exhalation valve is maintained relatively closed and the patient is allowed to exhale the gases in the patient's airway and lungs, pass the patient's vocal cords and out of the patient's mouth, thereby facilitating the patient's ability to speak. The method also includes (c) monitoring a pressure within at least one of the passages during the exhalation phase, and (d) determining whether a circuit disconnect or an occlusion exists based on the pressure monitoring.

It is a further object of the present invention to provide a patient ventilator assembly that is capable of operating in a speaking mode that allows the patient to speak while receiving the ventilation therapy and that monitors for anomalies to maximize the safety of the ventilator while in the speaking mode. This object is achieved according to one embodiment of the present invention by providing a patient ventilator assembly that includes a conduit adapted to be connected to an exterior open end of an endotracheal tube. The conduit includes inhalation and exhalation passages communicating with one another. The patient ventilator assembly also includes inhalation and exhalation valves in the inhalation and exhalation passages, respectively, and a pressure sensor adapted to monitor a pressure within at least one of the passages during the exhalation phase. A controller controls the inhalation valve and the exhalation valve so as to provide repetitive respiratory cycles, each respiratory cycle including an inhalation phase and an exhalation phase. During the inhalation phase the inhalation valve is relatively open and the exhalation valve is relatively closed and a flow of gas is allowed to pass through the inhalation passage and the tube into the patient's airway and lungs. The controller is further adapted to determine whether a circuit disconnect or an occlusion exists based on the monitored pressure.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various FIGS. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1A:
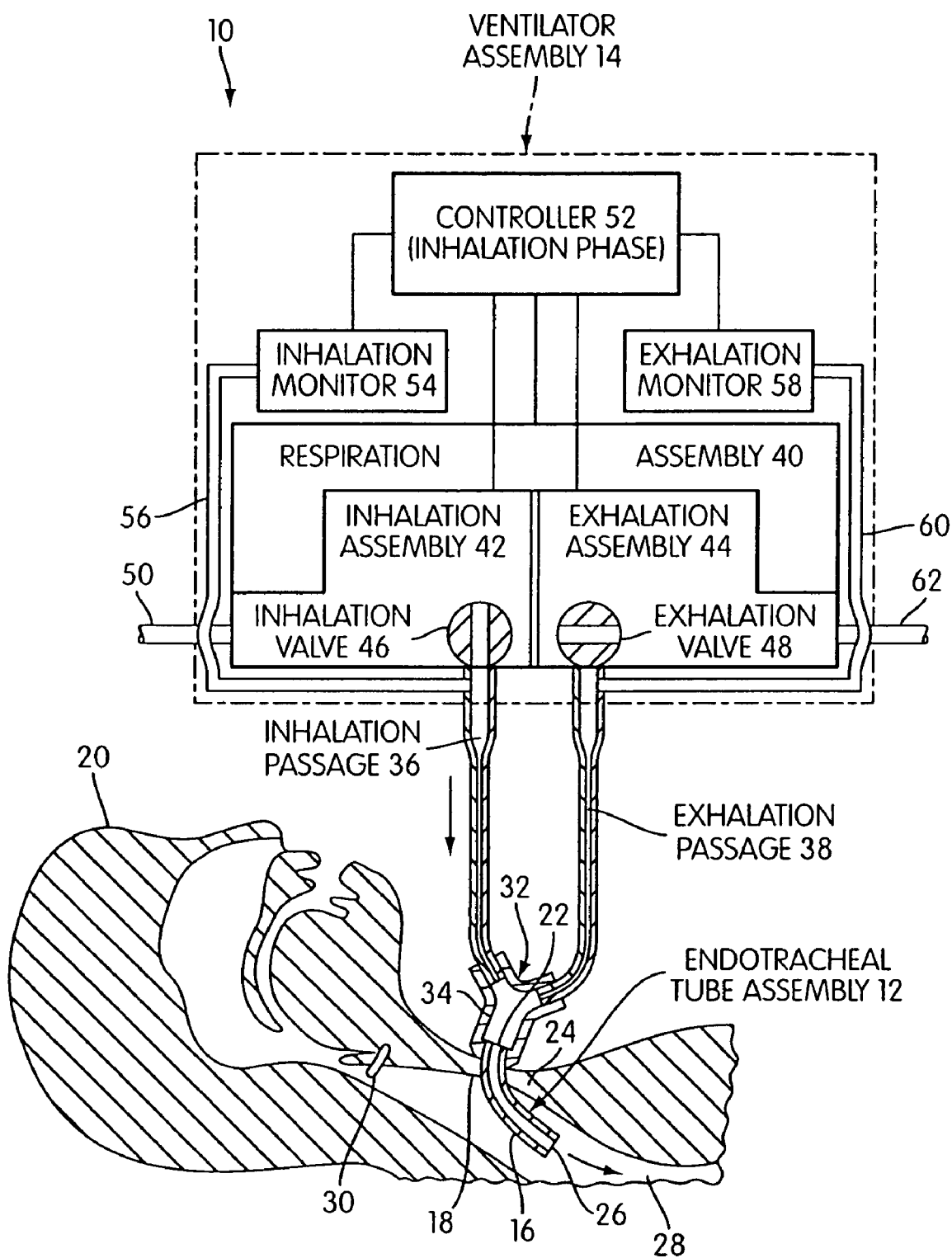
FIG. 1A is a partially schematic view of an embodiment of a ventilating apparatus according to one aspect of the invention, the apparatus being shown operatively connected with a patient with arrows indicating the direction of gas flow when the valves and controller are in an inhalation phase.

Referring now more particularly to FIGS. 1A, 1B, 2A, 2B, and 3 (or "FIGS. 1-3" for short) of the drawings, there is shown a ventilating apparatus, generally indicated at 10, embodying the principles of the present invention. Ventilating apparatus 10 includes, in general, an endotracheal tube assembly, generally indicated at 12, and a ventilator assembly, generally indicated at 14.

Endotracheal tube assembly 12 includes an endotracheal tube 16, constructed, for example, in accordance with the principles disclosed in the incorporated '356 patent. Endotracheal tube 16 is constructed and arranged to be mounted in a trachea 18 of a patient 20, as shown in FIGS. 1-3, so that an exterior open end 22 is suitably fixed in position exteriorly of the patient's neck 24 and an interior open end 26 communicates with the patient's airway and lungs 28 at a position below the patient's vocal cords 30.

Figure 2A:
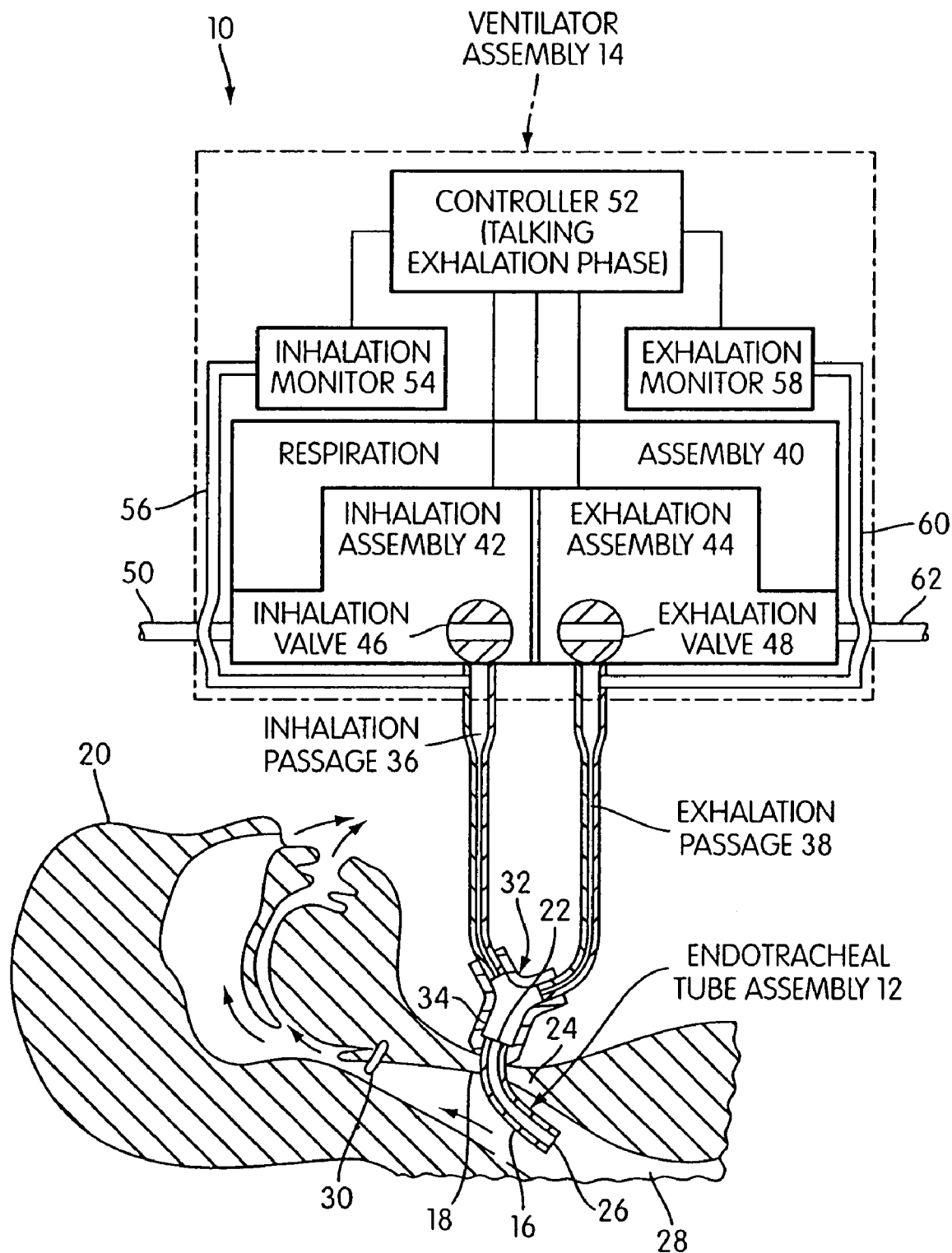
FIG. 2A is a partially schematic view of the embodiment of FIG. 1A, but showing arrows indicating the direction of flow when the valves and controller are in a talking mode exhalation phase.
Figure 2B:
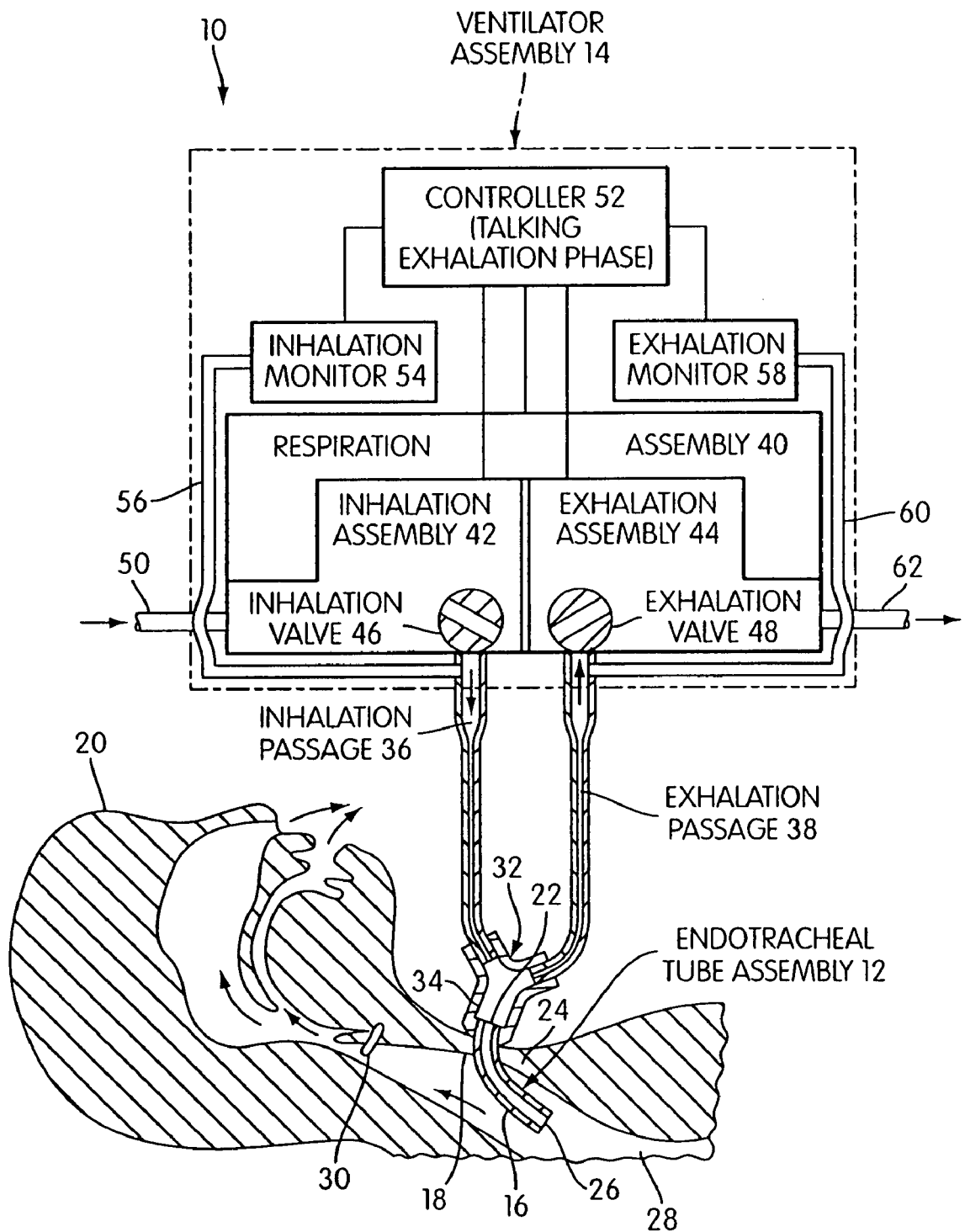
FIG. 2B is a view similar to 2A, but showing a partially closed exhalation valve and a partially closed inhalation valve.
Figure 3:
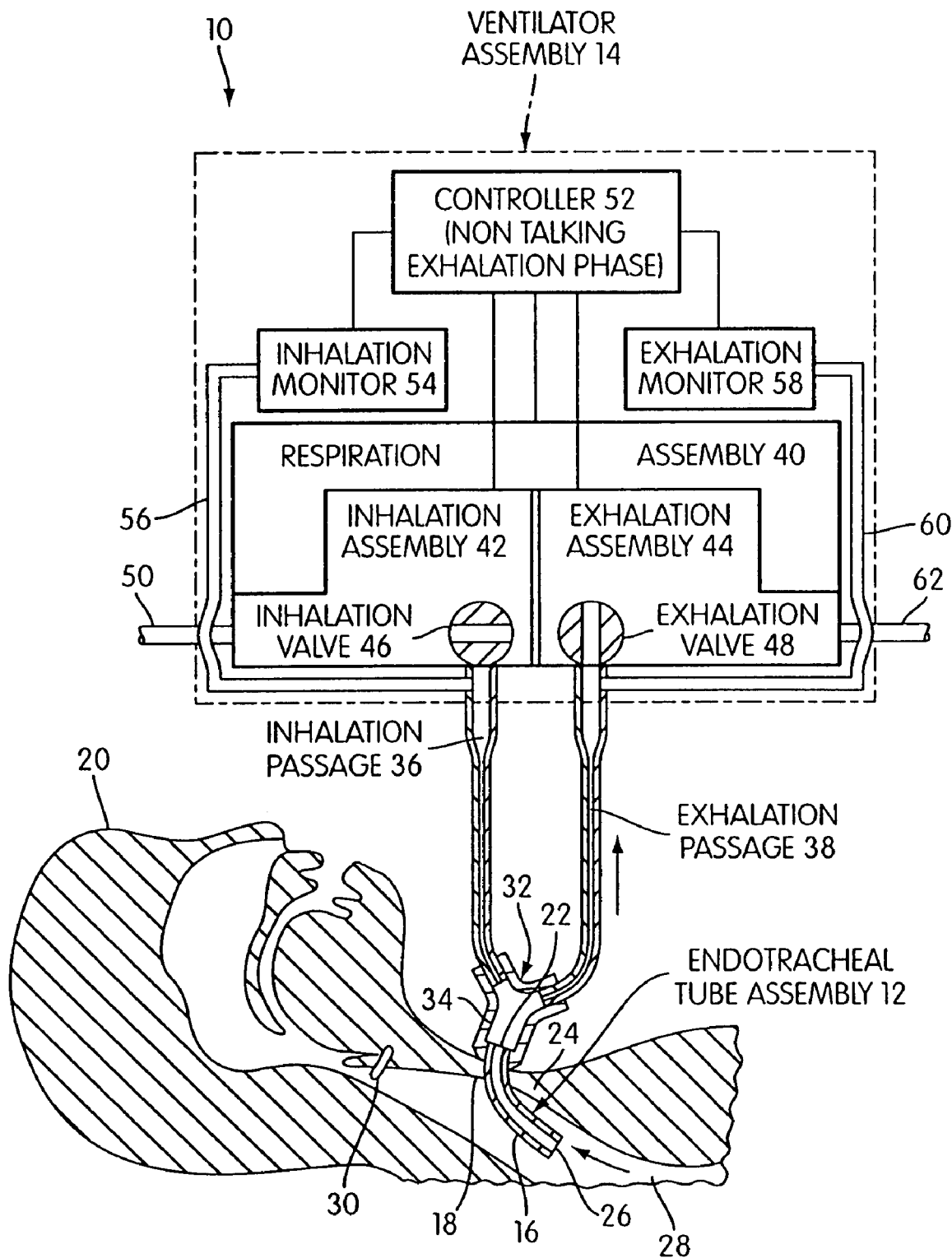
FIG. 3 is a partially schematic view of the embodiment of FIG. 1A, but showing arrows indicating the direction of flow when the valves and controller are in a non-talking mode exhalation phase.

In FIGS. 1-3, endotracheal tube 16 is shown as being devoid of a check valve, often referred to as the talking valve, such as the one disclosed in the '356 patent.

Ventilator assembly 14 includes a conduit assembly, generally indicated at 32, which includes a Y fitting 34 and tubing portions forming an inhalation passage 36 and an exhalation passage 38, as will be described below. The stem of Y fitting 34 is connected over exterior open end 22 of endotracheal tube 16 so that endotracheal tube is devoid of a check valve and communicates with conduit assembly 32 for gaseous flow therethrough in either direction.

One branch of the Y fitting is connected with the tubing or conduit section defining inhalation passage 36 and the other branch of the Y fitting is connected with the tubing or conduit section defining exhalation passage 38. As can be seen from FIGS. 1-3, Y fitting 34 serves to communicate inhalation passage 36 and exhalation passage 38 with one another.

Conduit assembly 32 thus far described is disposed exteriorly of ventilator assembly 14, as indicated by broken lines in FIGS. 1-3. Ventilator assembly 14 houses a respiration assembly 40 therein, which includes an inhalation assembly 42 and an exhalation assembly 44. In FIGS. 1-3, inhalation assembly 42 and exhalation assembly 44 of respiration assembly 40 are shown schematically in a block diagram. The gas flow components included in inhalation and exhalation assemblies 42 and 44 of respiration assembly 40 can be of conventional construction. A specific disclosure of one embodiment of the components used in accordance with the principles of the present invention is disclosed in the '449 patent.

As illustrated, inhalation assembly 42 includes a controllable inhalation valve 46 that communicates with inhalation passage 36, and exhalation assembly 44 includes a controllable exhalation valve 48 that communicates with exhalation passage 38.

Valves 46 and 48 are preferably controlled electronically by a controller 52 and are capable of being controlled to move between fully closed and fully open and any position of partial opening therebetween. Valves 46 and 48 can be of any suitable type for ventilator applications, such as proportional solenoid type valves, or stepper motor driven type, just for example.

Respiration assembly 40 is constructed and arranged to be controlled to provide repetitive respiratory cycles. Each respiration cycle includes an inhalation phase during which inhalation valve 46 is open and exhalation valve 48 is closed. During each inhalation phase, inhalation assembly 42 is controlled by controller 52 to cause a flow of gas to pass through the open inhalation valve 46, inhalation passage 36, endotracheal tube 16 into the patient's airway and lungs 28. In one embodiment, the flow of gas includes air and oxygen mixed by inhalation assembly 42 from a supply of air drawn through an inlet 50 of inhalation assembly 42 and a supply of oxygen contained within inhalation assembly 42. However, any known source of gas can be used and communicated through inhalation passage 36 via inhalation valve 46.

Each respiration cycle also includes an exhalation phase during which inhalation valve 46 is closed or partially closed (i.e., "relatively" closed as discussed later).

As best shown in FIGS. 2A and 2B, in accordance with an embodiment of the invention, ventilating apparatus 10 is adapted to be operated in a "speaking mode" in which exhalation valve 48 is controlled by controller 52 to remain in its relatively closed position, or to dynamically control the pressure in conduit assembly 32 in accordance with a desired pressure profile, during the exhalation phase, with the pressure profile being based upon the objective of enhancing the patient's ability to speak. This control of exhalation valve 48 enables the exhalation phase to be one in which the ability of the patient to talk is facilitated, even though there is no check valve embodied in endotracheal assembly 12 or conduit assembly 32. Thus, during the exhalation phase, when the patient is able to exhale the breathable gas introduced into the patient's airway and lungs in the preceding inhalation phase, the relatively closed inhalation and exhalation valves 46 and 48 prevent flow therebeyond, or are controlled to achieve a pressure profile in conduit assembly 32, so that the exhaled gas must flow passed the patient's vocal cords 30 on its way out of the patient's mouth, thus facilitating the patient's ability to talk, as shown by the arrows in FIGS. 2A and 2B.

Figure 1B:
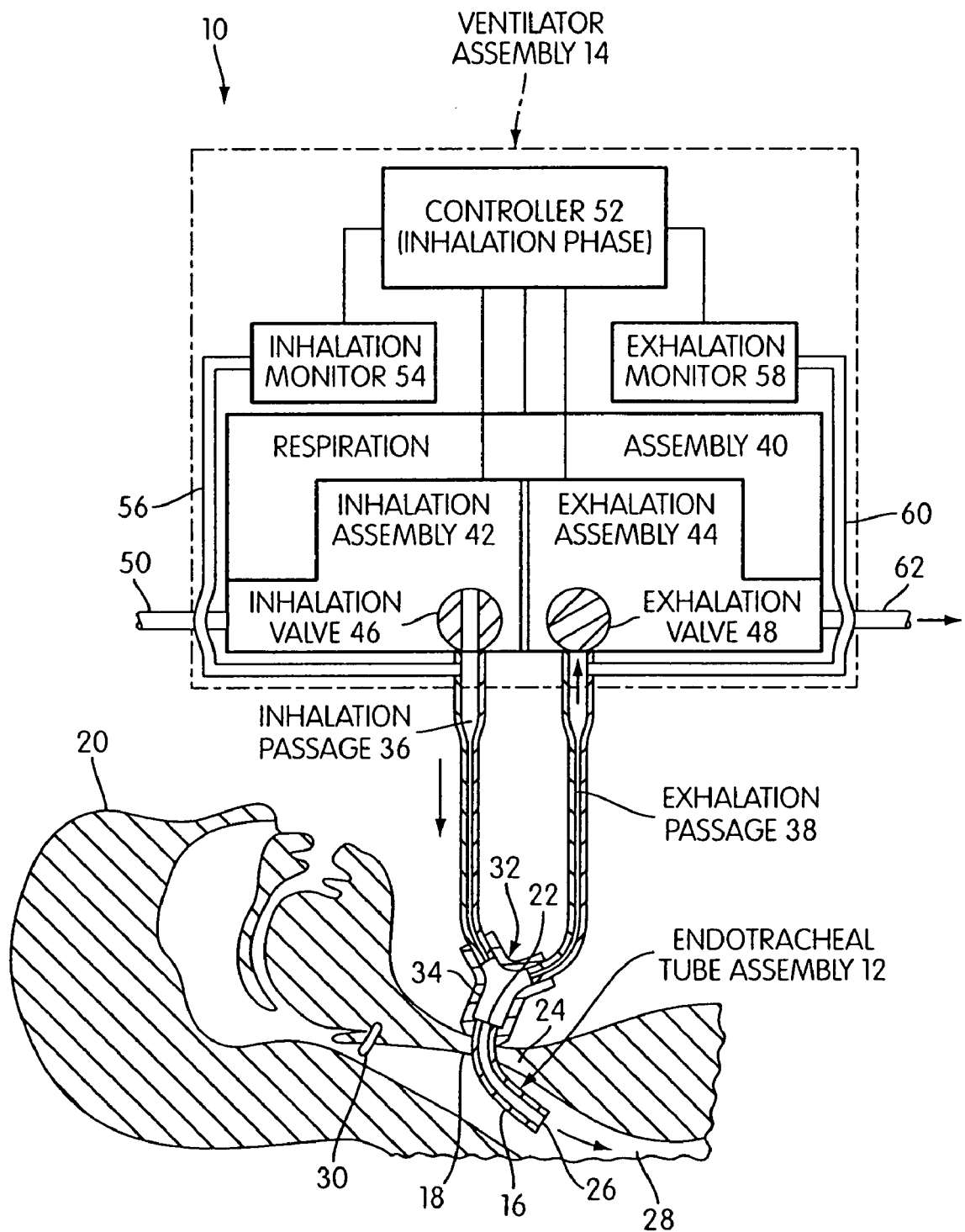
FIG. 1B is a view similar to 1A, but showing a partially closed exhalation valve.

It should be appreciated that in instances in which the inhalation valve or exhalation valve is disclosed herein as being "closed" or "open," this is not meant to necessarily refer to an absolute or fully open or fully closed valve (although it may), but rather a relational open or closed valve. In other words, for example, when the exhalation valve is "closed", this does not mean that it is completely closed to prevent any gas passage therethrough, as shown in FIGS. 1A and 2A. Rather, the exhalation valve may be partially closed, but closed sufficiently to achieve its desired functionality (as shown in FIGS. 1B and 2B). Thus, for example, a "relatively closed" or "relatively open" exhalation valve means a relatively closed position and a comparatively, relatively open position, respectively, as it relates to that particular valve. Similarly, a "closed" or "open" inhalation valve refers to two relative positions of the inhalation valve, wherein one position is relatively closed or relatively open with respect to the other. Thus, the term "relatively closed" as used herein is intended to convey this broad understanding and meaning.

In the inhalation phase, for example, the exhalation valve need not be fully closed, but may be closed only enough to enable a desired pressure to build within conduit assembly 32 and the patient's lungs. Similarly, in the inhalation phase, the inhalation valve need not be fully open, but may be open only enough to draw sufficient gas into conduit assembly 32 and patient's lungs to enable the patient to breath (not shown in the FIGS.). Similarly, in the exhalation phase, the inhalation valve need not be fully closed, but may be partially closed (see FIG. 2B), and the exhalation valve need only be closed sufficiently to maintain a desired profile of pressure in conduit assembly 32 (see FIG. 2B).

In one embodiment, the degree of opening and closing of the exhalation valve and/or inhalation valve is dynamically controlled by controller 52. Specifically, exhalation monitor 58 and/or inhalation monitor 54 can be used to monitor pressure throughout, or periodically during, the inhalation and/or exhalation phase and send a signal to controller 52 to continuously or intermittently send signals to open and/or close exhalation valve 48 and/or inhalation valve to a desired degree, based on a desired pressure to be provided within conduit assembly 32 or desired bleed rate through associated valve 46 and/or 48 at any point in the breathing cycle, or based upon the talking or non-talking mode of operation. In one embodiment, an encoder or any type of transducer can be used to measure the degree of valve opening and send feedback signals back to controller 52.

In one embodiment, during the inhalation phase, exhalation valve 48 is relatively closed (i.e., closed sufficiently to allow a desired amount of breathable gas to be provided to the patient), but may be only partially closed so as to be able to bleed excess gas (e.g. between about 3 to 7 liters per minute) through outlet port 62 (see FIG. 1B). In addition, inhalation valve 46 may be fully open or partially open, but in any event, relatively open in comparison when it is in the closed or relatively closed positions.

In one embodiment, during the exhalation phase, the exhalation valve and the inhalation valves are relatively closed, but one or both valves can be partially closed (see FIG. 2B) to control the level or pressure in conduit assembly 32. For example, in one embodiment it may be desirable to maintain the pressure in conduit assembly 32 above a specified threshold, such as, in one embodiment, 5 centimeters of water. Such control is often referred to as positive and expiratory pressure (PEEP), which can be used in the present invention, and as disclosed in U.S. Pat. No. 6,823,866, hereby incorporated by reference in its entirety. This method can be used to keep pressure within conduit assembly 32 above a certain level to keep the patient's airway open and/or enhance the patient's ability to speak.

It will be noted that while there is no flow through the communicating inhalation and exhalation passages 36 and 38 when valves 46 and 48 are closed in the exhalation phase, the communication provided by endotracheal tube 16 is such that passages 36 and 38 reflect the airway pressure during the exhalation phase just as they do during the inhalation phase.

In one embodiment controller 52 may be a programmable microprocessor and, as noted above, serves to control the operation of respiration assembly 40 in providing the repetitive respiration cycles, including control of inhalation assembly 42 and inhalation valve 46 thereof and exhalation assembly 44 and exhalation valve 48 thereof.

Controller 52, in its control of the overall operation of ventilator assembly 14, uses data relating to the measured pressure within the patient's airway as reflected in inhalation and exhalation passages 36 and 38. While the measured data could be obtained from a single monitor, in the illustrated embodiment two monitors are provided, including a inhalation monitor 54 communicated with inhalation passage 36 by suitable tubing 56, and a separate exhalation monitor 58 communicated with exhalation passage 38 by suitable tubing 60. In one embodiment, monitors 54 and 58 use pressure transducers capable of sensing the pressure conditions of the communicating passage and converting the sensed pressure condition into a discrete signal capable of being received and used by controller 52. Controller 52 opens and closes valves 46 and 48 based upon monitor 54 and/or monitor 58, the output of which can be used to detect the phase of respiration that the patient is in. That is, the monitors track the pressure within the patient's lungs throughout the breathing cycle to control opening and closing of valves 46 and 48.

In one embodiment, the controller uses two distinct algorithms, one for controlling exhalation valve 48 and the other for controlling inhalation valve 46. In another embodiment, the controller comprises two separate control units or control modules, one for controlling each valve and connected with at least one of monitors 54 and 58.

From the above, it will be understood that controller 52 is programmed so that during each exhalation phase, a talking mode is entered in which the exhalation valve remains closed or partially closed, as previously described.

In addition, the controller is programmed so that during the exhalation phase, a non-talking mode may be entered into, in which the exhalation valve is opened. In this non-talking mode (or "first" mode), the gas in the patient's airway and lungs at the end of the inhalation phase is allowed to flow through endotracheal tube 16, open exhalation valve 48 and out of an outlet 62 provided by exhalation assembly 44, as shown by the arrows in FIG. 3. The non-talking exhalation phase is entered into when monitor 54 and/or 58 sends a signal to controller 52 indicating a prescribed condition. For example, if monitor 54 and/or 58 detects that pressure in conduit assembly 32 is not being reduced at an expected rate, it may be indicative of a blockage (e.g., gas is being forced back into conduit assembly 32 rather than past the vocal chords) or airway occlusion. In this case, exhalation valve 48 will be open to allow gas to escape from the patient's lungs.

From the above, it can be seen that ventilating apparatus 10, as described above, facilitates the ability of the patient to talk when in the talking mode (or "second" mode) as shown in FIG. 2, and also provides a non-talking ventilation mode (see FIG. 3) merely by operation of controller 52 of FIG. 3. It should be appreciated that some talking may be possible in the first (or "non-talking") mode, although it may not be as conducive.

Referring now more particularly to FIGS. 4A, 4B, 5A and 5B (or "FIGS. 4 and 5" for short), there is shown therein an alternate embodiment. In this embodiment, endotracheal tube assembly 12 includes a conventional check valve 64 in conduit assembly 32. This embodiment demonstrates that the feature of enabling controller 52 to select a mode in which exhalation valve 48 is maintained in a relatively closed position during the exhalation phase can secure advantages even when a conventional check valve 64 is employed.

In the embodiment of FIGS. 4 and 5, controller 52 operates in a talking mode similar to the talking mode described above. The difference is that gas flow communication from the patient to ventilator assembly 14 during the exhalation phase is cut off at check valve 64 rather than at the relatively closed exhalation valve 48. If controller 52 actually functioned to open exhaust valve 48 during the exhalation phase as in the FIG. 3 non-talking mode, the pressure in exhalation passage 38 would simply be at atmospheric pressure during the exhalation phase so that exhalation monitor 58 would not be monitoring the patients airway pressure during the exhalation phase.

Figure 4A:
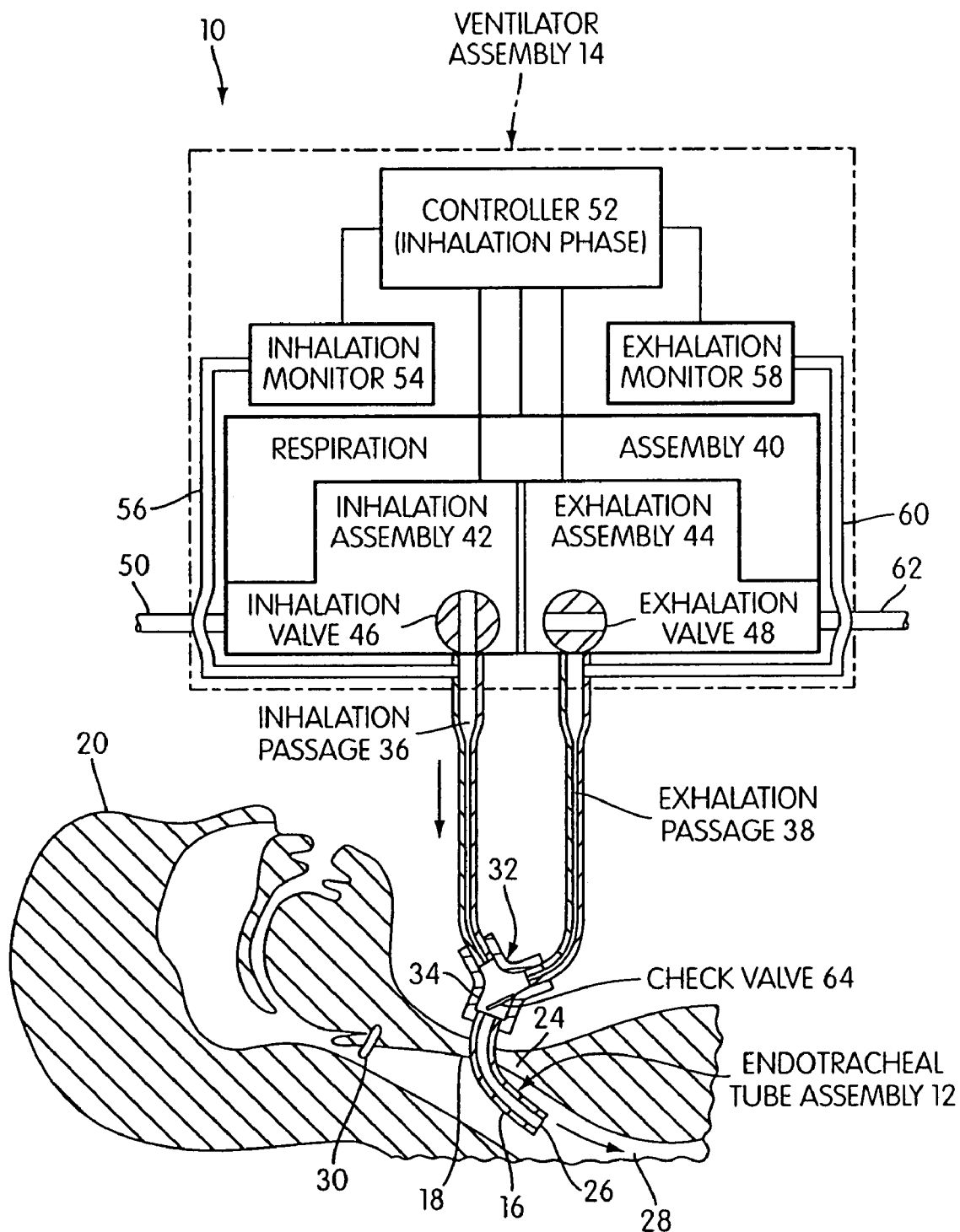
FIG. 4A illustrates another embodiment of the present invention wherein the endotracheal tube, rather than being devoid of a check valve as in FIG. 1A, has a check valve in the open end thereof.
Figure 4B:
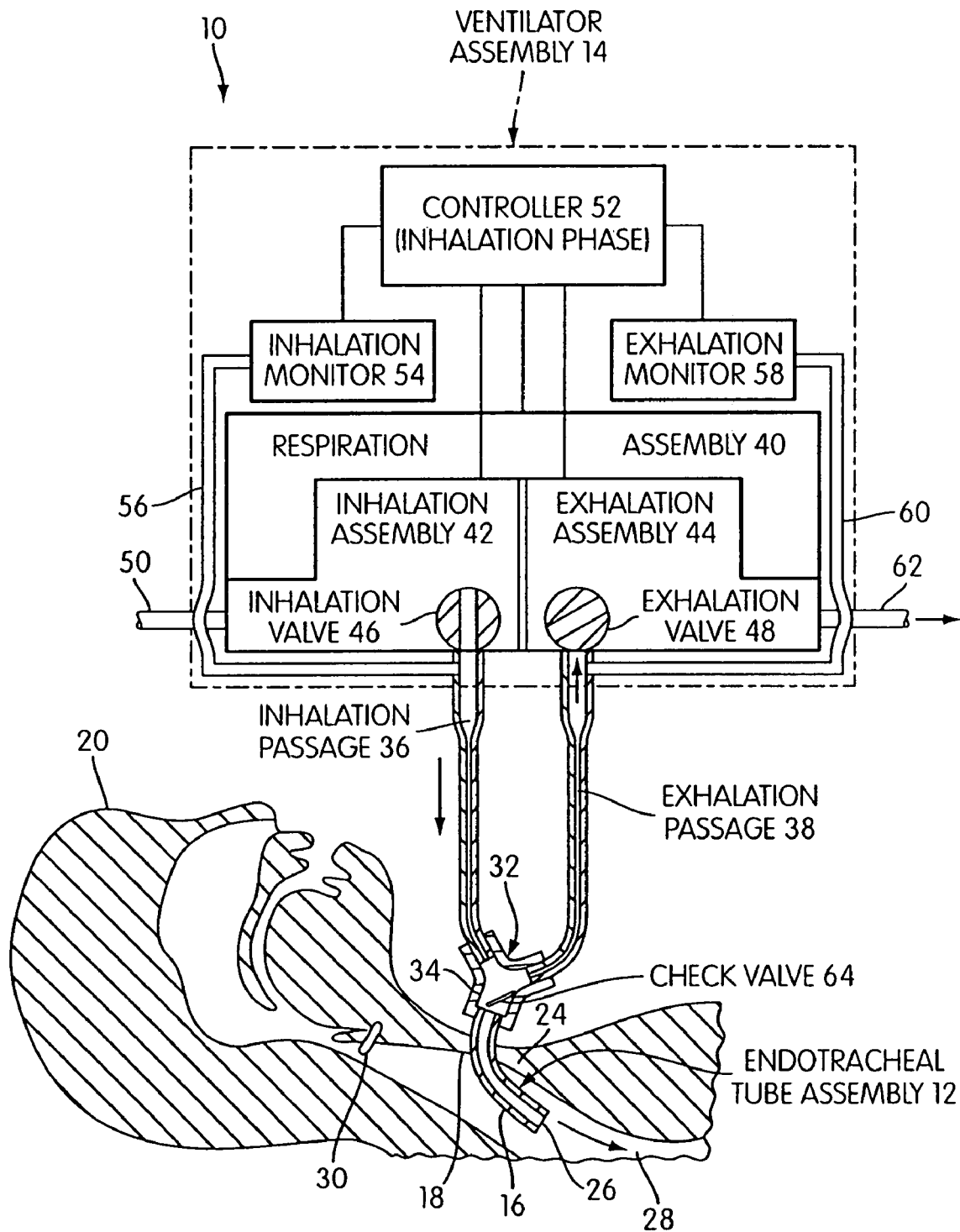
FIG. 4B is a view similar to 4A, but showing a partially closed exhalation valve.
Figure 5A:
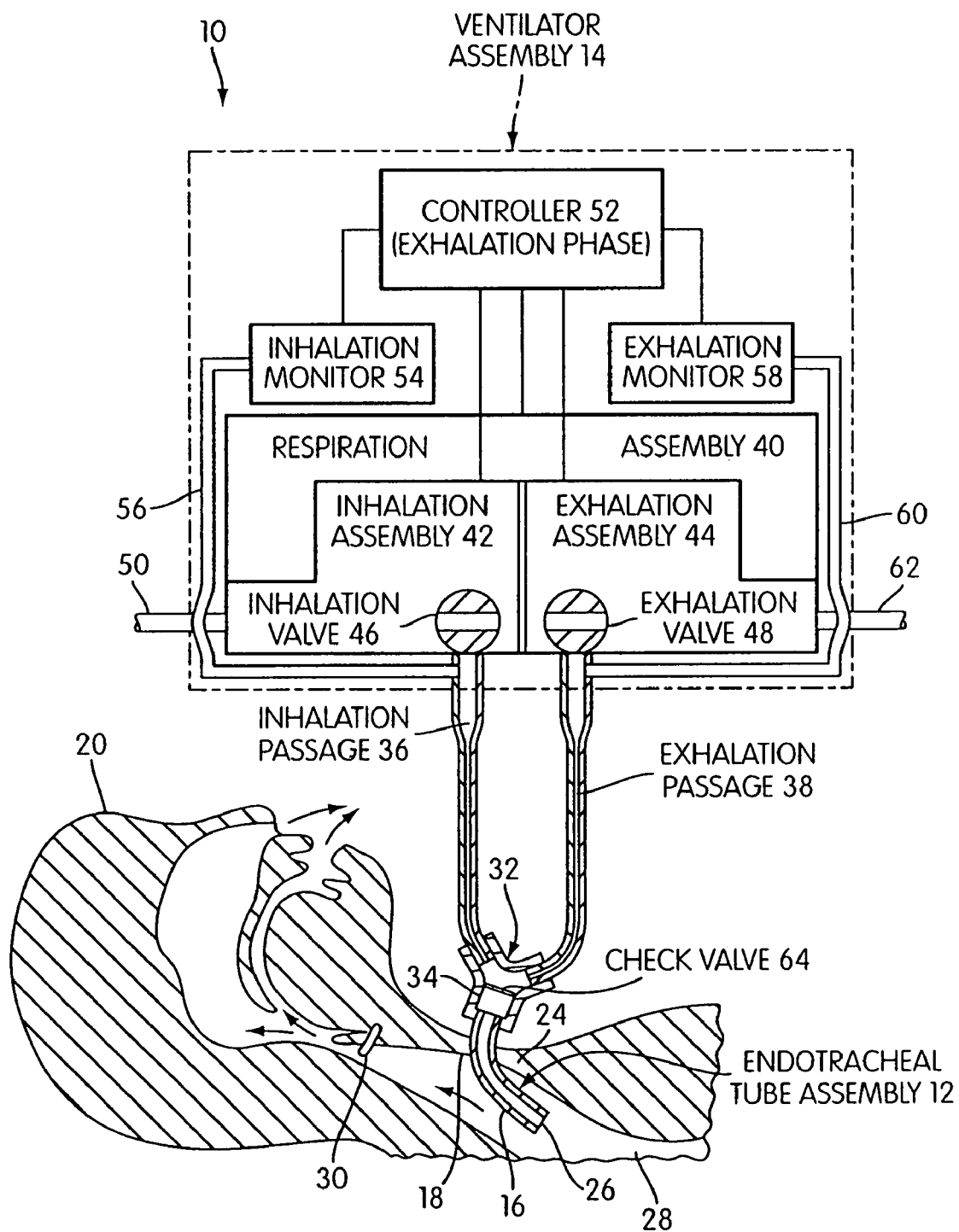
FIG. 5A is a view similar to FIG. 4A, but showing arrows indicating the direction of flow when the valves and controller are in an exhalation phase.
Figure 5B:
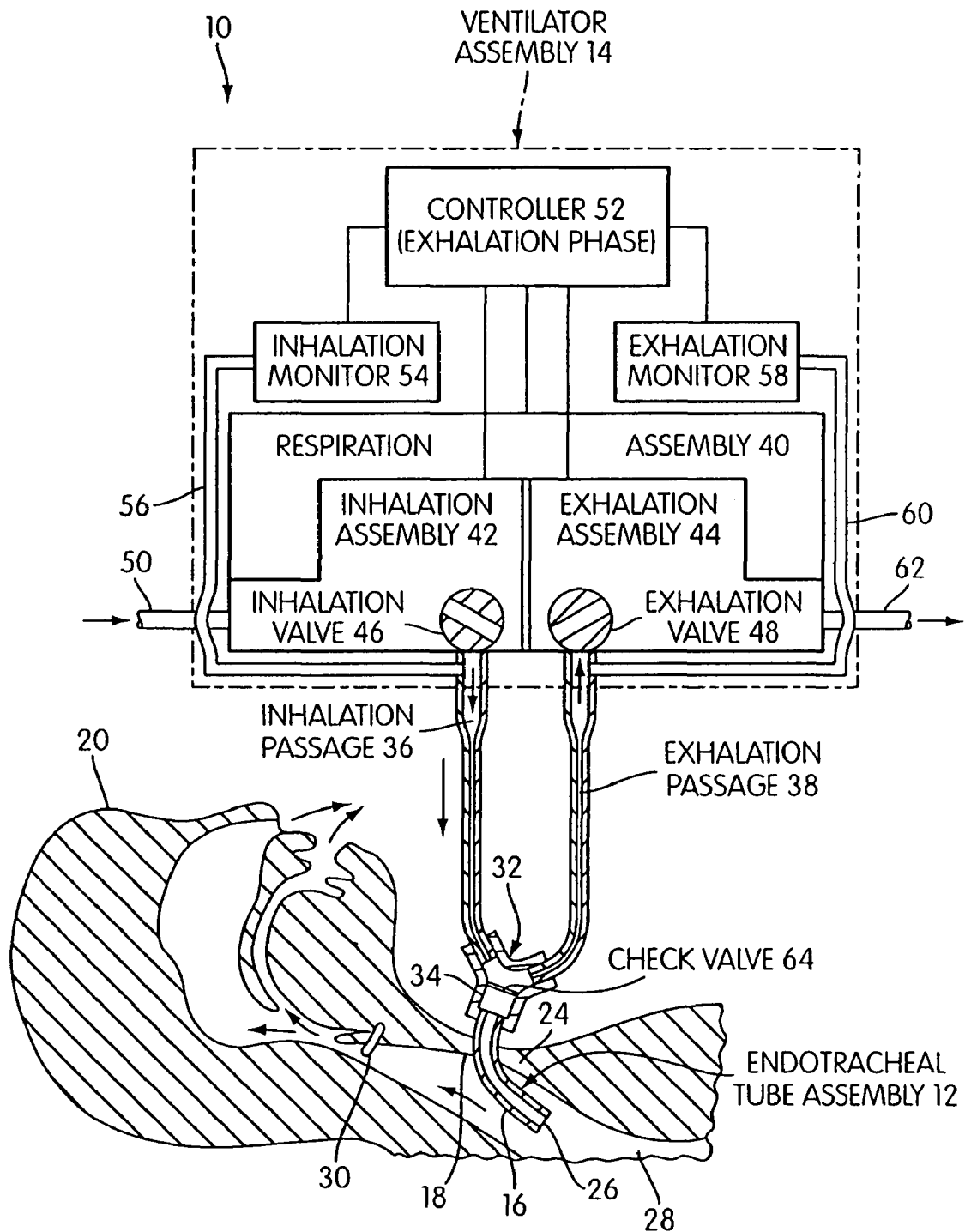
FIG. 5B is a view similar to FIG. 5A, but showing partially closed exhalation and inhalation valves.

Note that FIG. 4B is functionally the same as 4A, but showing a partially closed exhalation valve, while FIG. 5B is functionally the same as FIG. 5A, but showing partially closed inhalation and exhalation valves.

As noted above, controller 52 will regulate exhalation valve 48 so as to be relatively closed during the exhalation phase, when the inhalation valve 46 is relatively closed, and the pressure in exhalation passage 38 will be generally equal to the patient's airway pressure throughout the exhalation phase. Since this pressure reduces in the patient's airway as the exhalation phase proceeds, the exhalation monitor can continue during the exhalation phase to monitor the patients reducing airway pressure. Because the closed (or partially closed) inhalation valve 46 and closed (or partially closed) exhalation valve 48 will maintain the pressure within the communicating inhalation passage 36 and exhalation passage 38 at or slightly above the pressure in the patient's lungs during the exhalation phase, and because this pressure is approximately balanced with the pressure in the patient's lungs through operation of the check valve 64, exhalation monitor 58 (and/or inhalation monitor 54) is/are able to effectively approximate the pressure in the patent's lungs at all times during the exhalation phase. Consequently, as the patient's airway pressure diminishes during the exhalation phase, the pressure closed within communicating passages 36 and 38 will continue to equalize with the patient's airway pressure during the exhalation phase. Exhalation monitor 58 is thus monitoring the patient's airway pressure during the exhalation phase rather than atmospheric pressure, as would be the case if the exhalation valve were to open.

Figure 6:
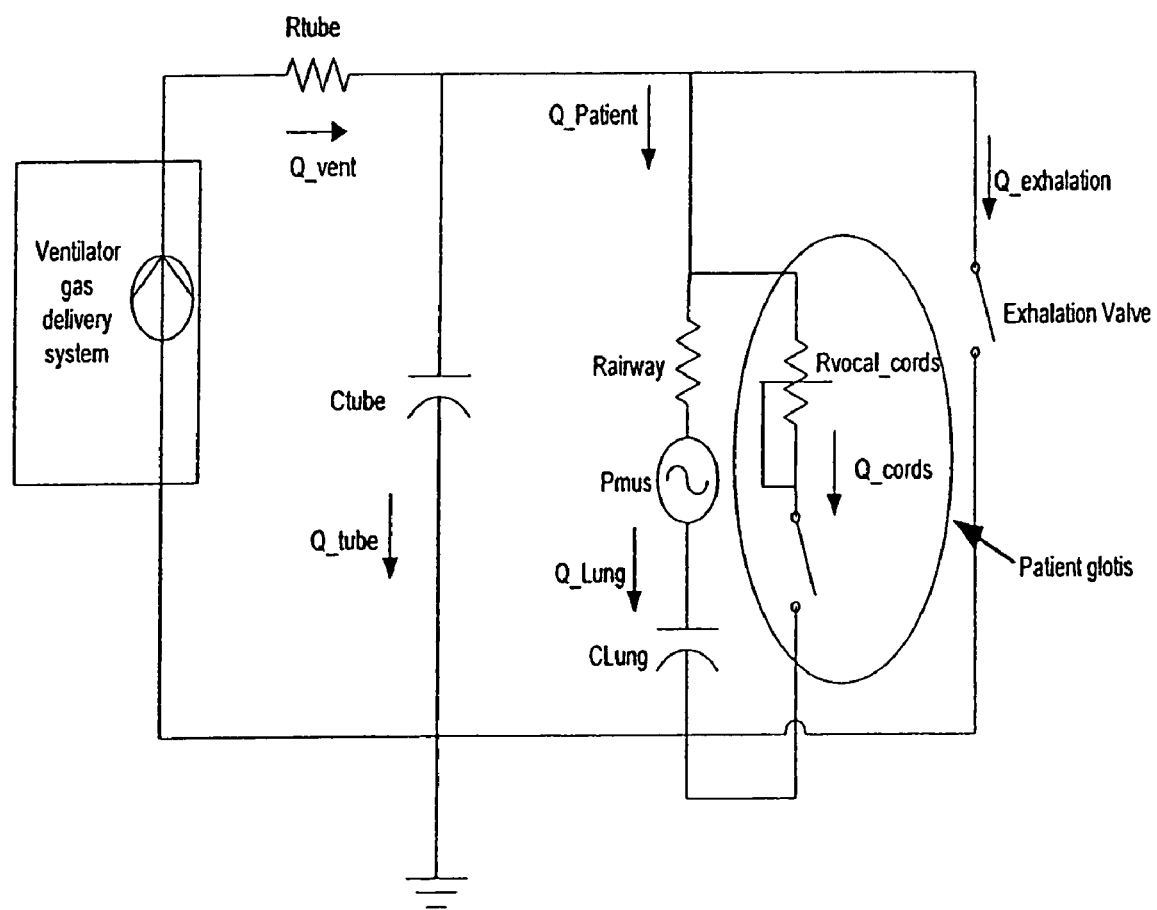
FIG. 6 schematically depicts the system of FIGS. 1 and 2 as an analogous electric circuit diagram, and showing an arrangement in which the exhalation valve is completely closed during the inhalation and exhalation phases.

FIG. 6 schematically depicts the system of FIGS. 1 and 2 as an analogous electrical circuit diagram.

In FIG. 6, the various components of the system shown in FIGS. 1 and 2 are depicted as electrical symbols as known in the art, each labeled with a descriptive word or descriptive abbreviation. The descriptive abbreviations are as follows: Rvocal_cords refers to the patient's vocal cord resistance. Rvocal_cords is shown as a variable resistor to show the variable resistance generated by the vocal cords (for example, higher pitch sounds generate greater resistance). Rairway refers to the patient's airway resistance. Rtube refers to the patient's circuit tubing resistance or conduit resistance. Ctube refers to the patient's circuit tubing compliance or conduit compliance, which can be measured as a capacitance, or the volume of tubing divided by the pressure in the tubing. Clung refers to the patient's lung compliance. Pmus refers to the pressure created in the patient's lungs by the patient's muscles, and illustrated as an alternating pressure generated by the patient through the patient's muscle action (e.g., patient's diaphragm, intercostal muscles, pectoral muscles, etc.).

The prefix letter Q refers to a quantity of gas flow delivered by the ventilator (Q_vent) or by the patient during the exhalation phase (Q_exhalation). The Q prefix also refers to a quantity of gas flow delivered (1) to the conduit or tubing system (Q_tube), (2) to the patient (Q_patient), (3) to the patient's lungs (Q_lung) and (4) to the patient's vocal cords (Q_cords).

As shown in FIG. 6, gas flow is delivered by the ventilator (Q_vent) during the inhalation phase of the breathing cycle. Because the exhalation valve is closed (i.e., switch open) during this phase, gas is delivered to the patient (Q_patient) as well as the tubing system (Q_tube). During the inhalation phase, the flow through the vocal cords (Q_cords) is typically zero, as the patient's glottis is closed (represented by the open switch next to Q_cords in FIG. 6) so the gas (Q_Lung) is delivered to the patient's lungs. However, it should be appreciated that in some instances during the inhalation phase, the gas being delivered by the ventilator can be used for speech purposes by the patients, and so the flow through vocal cords is not zero.

It should be appreciated that the open switch in FIG. 6 labeled "Exhalation Valve" represents an arrangement wherein the exhalation valve is completely closed for both inhalation and exhalation phases. This switch can be replaced by a variable resistor to reflect arrangements wherein the exhalation valve may be partially or relatively closed during exhalation and/or inhalation phases.

Generally, the exhalation phase of the breathing cycle is when talking is facilitated. Talking is accomplished by increasing the pressure in the lung via the thoracic muscle recoil forces as well as diaphragmatic muscle activity. During speech, the direction of Q_Lung is reversed and leaves the patient through the vocal cords. Modulation of the vocal cords (i.e., vocal cords' resistance variation) is responsible for the cords vibrations which ultimately become speech.

During the exhalation phase, the ventilator's exhalation valve remains closed (or partially closed), and in this way, the majority of the gas flow is redirected towards the vocal cords during speech. During exhalation, a small amount of gas may flow towards the tubing system compliance. This compliance, typically less than 2 ml/cmH$_2$O, being small compared to the patient Lung compliance (Clung) uses a few milliliters of the gas volume exhaled by the patient.

The embodiments just described without the speaking valve (check valve) have several advantages, including, but not limited to, the following:

1) Allows detection of inflated tracheotomy tube cuffs. This is possible since the ventilator pressure sensors are able to monitor the pressure in the tubing system and this pressure in turn reflects the pressure in the patient's airway and lungs.

2) Allows assessment of the patient's airway pressure during exhalation so that stacking of breaths is avoided. This is not practical in embodiments using the speaking valve, since the valve blocks the pneumatic communication with the ventilator's pressure transducers.

3) Allows for strong patient coughs without interference from a one way valve's membrane, since no valve is used.

4) Allows aerosol treatments without the need to take out the speaking valve.

5) Allows suctioning without the need to take out the speaking valve.

6) Avoids the need to take out the speaking valve to prevent the valve's disc/membrane from becoming clogged with sputum, since no speaking valve is required.

Note that embodiments where the speaking valve is present, the volume of gas trapped in the tubing circuit can only escape through the speaking valve. Gas flow through the speaking valve is possible only if there exists a pressure differential across the valve. Thus, monitoring of the pressure in the patient's airway and lungs via monitoring of the tubing system pressure is possible, so long as the pressure in conduit assembly 32 is greater than or equal to the pressure in the patient's lungs, which is the manner of operation of the present invention.

The present inventor recognized that during the speaking mode, as described above, it is desirable to ensure that the ventilation system operates in a way that remains safe for the user. For example, if the tracheostomy tube's cuff is not deflated or the airway around the tracheostomy tube becomes occluded while in the speaking mode, gas may not be able to leave the patient's lungs. Also disconnection of the patient circuit tube may prevent an effective operation of the ventilator in ventilating the patient. Thus, the present invention seeks to detect occlusions so as to prevent the pressure in the patient's lungs from exceeding a given threshold as well as to prevent asphyxiation, and to detect disconnections or loosing of the components of the ventilator assembly or the endotracheal tube assembly.

Detecting disconnections or loosing of the components of the ventilator assembly or the endotracheal tube assembly is accomplished by monitoring the pressure of the ventilator circuit at or near the patient (Py). It should be noted that monitoring the pressure can be accomplished by providing a pressure sensor at or near the patient, such as on the wye (Y) connector, or the pressure monitoring can be accomplished by monitoring the pressure in the inhalation and/or exhalation passage. In a further embodiment, the pressure at or near the patient is approximated by measuring the pressure in the ventilator assembly and using conventional techniques to account for the pressure drop in the tubing and/or endotracheal tube assembly, for example by accounting for the pressure drop in the inhalation passage in the case of monitoring pressure in the inspiratory limb or by accounting for the pressure drop in the exhalation passage in the case of monitoring pressure in the expiratory limb.

While operating in the speaking mode, the exhalation valve remains closed during all phases of ventilation, i.e., during both inhalation and exhalation. In the absence of a disconnect or leak in the tubing circuit, the pressure in the tubing circuit and the patient's airways decays as a function of the level of gas exhaled through the patient's mouth and/or nose. The present inventor recognized that if a disconnect of the patient circuit and/or a significant leak in the patient circuit exists, once the level of gas delivery from the ventilator is cut below a threshold (i.e. 2 lpm), the pressure at the tubing circuit wye decays very fast to a value that is close to zero. More specifically, this rapid pressure decay occurs within the first 100 milliseconds of the initiation the exhalation phase of a breath and remains at this level for the remainder of the exhalation phase. The present invention makes use of this characteristic to detect/declare a circuit disconnect or leak (collectively referred to as a "circuit disconnect").

The present invention contemplates that the pressure is monitored using exhalation monitor 58 and the circuit disconnect or leak detection algorithm is implemented by controller 52. The total flow of gas provided from the ventilator is monitored by a flow sensor associated with the flow of inspiratory gas, such as a flow sensor disposed in series with the inspiratory circuit within ventilator assembly 14. In a further embodiment, the total flow ($Q_{tot}$) is based on both the flow of air ($Q_{air}$) monitored by a first flow sensor, and the flow of a supplemental gas ($Q_{O2}$), such as oxygen, monitored by a second flow sensor over a given period of time. That is, $Q_{tot}=Q_{air}+Q_{O2}$ and is a running average of these flows taken over a period of time, such as 50 msec. $Q_{tot}$ can also be compensated to any given criteria. For example, it is known to compensate the flow to a body temperature pressure saturated (BTPS) flow.

In an exemplary embodiment of the present invention, the system detects or determines when the patient is in the exhalation phase. Once the time elapsed since the start of the exhalation phase ($T_{exh}$) is greater than a predetermined value, such as 100 msec, and once the total flow $Q_{tot}$ is less than a predetermined amount, such as 2.0 lpm (at least once), the system monitors Py in order to detect whether there is a circuit disconnect or significant leak. In this exemplary embodiment, a peak pressure $P_{peak}$ is monitored. In this embodiment the peak pressure $P_{peak}$ is a peak value of the average pressure taken over a 50 msec moving window measured during exhalation, is monitored. Again, the identification of the peak value for the pressure starts once 100 msec of exhalation have elapsed and when $Q_{tot}<2$ lpm.

In the exemplary embodiment, a minimum pressure $P_{min}$ is also monitored. The minimum pressure $P_{min}$ corresponds to a minimum value for the average pressure measured over the 50 msec moving window during exhalation. The identification of this minimum value starts once 100 msec of exhalation have elapsed and when $Q_{tot}<2$ lpm at least once.

In an exemplary embodiment of the present invention, a circuit disconnect is declared if the following conditions exist:

1) $P_{peak}-P_{min}<P_{threshold1}$,
2) $P_{peak}<P_{threshold2}$,
3) The patient has not triggered the ventilator, and
4a) The pressure at the end of exhalation ($P_{end\_exh}$)≦1 cmH$_2$O, or
4b) The $P_{end\_exh}$≦the pressure at the start of exhalation ($P_{start\_exh}$)—a delta pressure.

Delta pressure is the higher of 1 cmH$_2$O or 50% of $P_{start\_exh}$. There are numerous techniques that are used to determine when the patient has triggered the ventilator. For example, U.S. Pat. No. 6,626,175, the contents of which are hereby incorporated by reference, teaches several such techniques. If the triggering criteria that are used to determine when the patient has transitioned from exhalation to inhalation are satisfied, the patient is deemed to have triggered the ventilator. It should be noted that triggering the ventilator can also occur automatically, i.e., via internal timing mechanisms without the patient's inspiratory effort.

The circuit disconnect criteria set forth above are provided to ensure that an actual disconnect has occurred. It is to be understood that other embodiments of the present invention do not require that all of these criteria be met. Conversely, still other conditions can be required depending on how aggressive or how reliable the circuit disconnect determination should be.

To create pressure stability in the tubing circuit, and, thus, allow for the detection of patient tubing disconnections, the present invention contemplates controlling the air and oxygen flow valves, i.e., inhalation valve 46, to close in such a manner so as to minimize pressure oscillations in the tubing system that would otherwise be induced by abrupt closure of the gas delivery valves. For example, these valves or valve can be closed using an exponential function trajectory so that they close "gently".

In an exemplary embodiment of the present invention, $P_{threshold\ 1}$ is set at 1.0 cmH$_2$O, and $P_{threshold\ 2}$ is set at 3.0 cmH$_2$O. It should also be noted that the value for these pressure thresholds need not corresponds to these specific values. The current threshold values are selected so that drift of the flow/pressure sensors does not cause an erroneous circuit disconnect determination.

The present invention further contemplates that the criteria for a circuit disconnect is tested throughout the entire exhalation phase. In addition, the present invention contemplates that a circuit disconnect will not be declared if a high inspiratory pressure (HIP) condition has occurred, or if an occlusion, as discussed below, has been declared during the breath.

If a circuit disconnect is detected, a variety of actions can be taken. For example, the ventilator can be programmed to sound a circuit disconnect alarm. The ventilator can also be programmed to continue to deliver ventilated breaths (based on the mode and breath type), at the scheduled times and with the exhalation valve closed during the breath's exhalation phases. The conditions for a circuit disconnect, as noted above, can tested on every breath. If the test proves false, i.e., no circuit disconnect is detected, in a later breath, the circuit disconnect alarm can be discontinued or reset. Of course, a log of the circuit disconnect event can be maintained.

The present invention contemplates several different techniques for detecting an occlusion of the patient's airway. As noted above, such an occlusion, whether partial or complete, during the speaking mode could adversely impact the ability to implement the speaking mode, the ability to ventilate the patient, and may expose the patient to excessive lung pressures.

In a first exemplary embodiment, an airway occlusion is declared if a high exhalation pressure condition is continuously detected over a predetermined period of time. For example, if a high exhalation pressure exists for 190 msec consecutively, an occlusion is deemed to exist. In this exemplary embodiment, a high exhalation pressure is defined as a detection of the pressure, as measured by the exhalation pressure sensor, that is higher than the High Inspiratory Pressure (HIP) limit, which is typically set by the caregiver.

In one embodiment, if a high exhalation pressure condition is detected for 190 milliseconds consecutively, the exhalation valve is opened immediately. The exhalation valve will close again at the start of the next inhalation and ventilation will resume with the exhalation valve closing during inhalations and opening during exhalation phases until the occlusion condition is manually reset by the user. Once the condition is reset, the exhalation valve operation returns to be closed, in both inhalation and exhalation phases, starting at the beginning of the next breath's inhalation.

It should be noted that the 190 msec period give above is based on the applicable standard (i.e. 60601-2-12 IEC:2001 (E); see clauses 50.105 and 50.106 titled Adjustable Pressure Limitation and High Pressure Alarm Condition respectively). Other time periods and high exhalation pressure levels are contemplated by the present invention and can be set or determined based on the needs of the patient or the judgment of the caregiver. The present invention also contemplates that the time period and high exhalation pressure can be adjustable, for example based on the ventilator settings, the condition of the patient, or any other input.

In a second exemplary embodiment, an airway occlusion is declared based on a comparison of the pressure at the wye with certain occlusion threshold criterion. That is, during the exhalation phase of mandatory breaths (i.e. volume controlled ventilation (VCV) or pressure controlled ventilation (PCV)), while in the speaking mode, the pressure at the wye is compared to occlusion threshold criterion. The comparison starts 100 msec after the reduced flow condition is reached, i.e., $T_{exh}$>100 msec and $Q_{tot}$<2 lpm at least once during the exhalation phase is met, and continues until the end of the exhalation phase.

In this embodiment, an airway occlusion is not declared if, during the exhalation phase, $P_{exh\_50}$<$P_{occl}$ for more than 100 msec, consecutively. $P_{exh\_50}$ corresponds to a 50 millisecond running average of the pressure measurements and is expressed in cmH$_2$O. The occlusion threshold criterion ($P_{occl}$), which is also expressed in cmH$_2$O, is calculated, every 5 msec (i.e. every control cycle (n) of the process), as follows:

$$P_{occl}=Po*\exp(-n*3*0.005/RT)-0.5, \qquad (1)$$

where:

Po=$P_{exh\_50}$ 100 msec after $Q_{tot}$ falls below 2 lpm for the first time.

RT=$T_{auoccl}$; where, $T_{auoccl}$=0.06*CL*$R_{occl}$ (given in seconds),

CL=Vt/Po=Patient's lung compliance (ml/cmH$_2$O),

Vt=Volume delivered by the ventilator during the inhalation phase (given in ml), $R_{occl}$=Po/$Q_{occl}$=Equivalent Occlusion Resistance (given in cmH2O/L/min), $Q_{occl}$=Maximum flow level expected to leave the patient's airway during an airway occlusion. $Q_{occl}$ is expressed in lpm and is calculated as follows:

$$Q_{occl}=1E-05*Po\,\hat{}\,3-0.0019*Po\,\hat{}\,2+0.1581*Po+0.2424. \qquad (2)$$

An airway occlusion alarm is declared if $P_{exh\_50} \geq P_{occl}$ for most of the exhalation, and this condition is met for two consecutive breaths. If $P_{exh\_50} \geq P_{occl}$ for most of the exhalation, a second inhalation is started, and, if during this inhalation, the pressure measured in the tubing system reaches a level greater or equal to the HIP Limit minus 1 cmH$_2$O (HIP−1), the gas delivery system interrupts the gas delivery activity, but the exhalation valve will remain closed for the duration of the next exhalation. If on the second consecutive exhalation, the $P_{exh\_50} \geq P_{occl}$ condition is valid for most of the exhalation, an airway occlusion is declared at the start of the following inhalation. In which case, the exhalation valve is opened and a new exhalation phase is declared. At the end of this additional exhalation phase, the exhalation valve is closed again at the start of the next inhalation, and ventilation resumes with the exhalation valve closing during inhalations and opening during exhalation phases until the occlusion condition is manually reset by the user. Once the condition is reset, the exhalation valve is closed in both inhalation and exhalation phases, starting at the beginning of the next breath's inhalation.

Figure 7A:
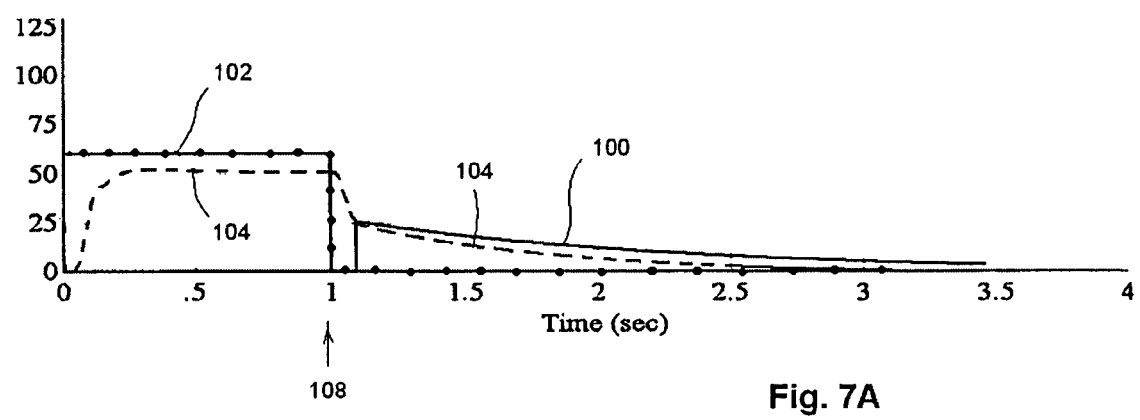
FIGS. 7A and 7B are graphs illustrating an occlusion detection technique according to one embodiment of the present invention.
Figure 7B:
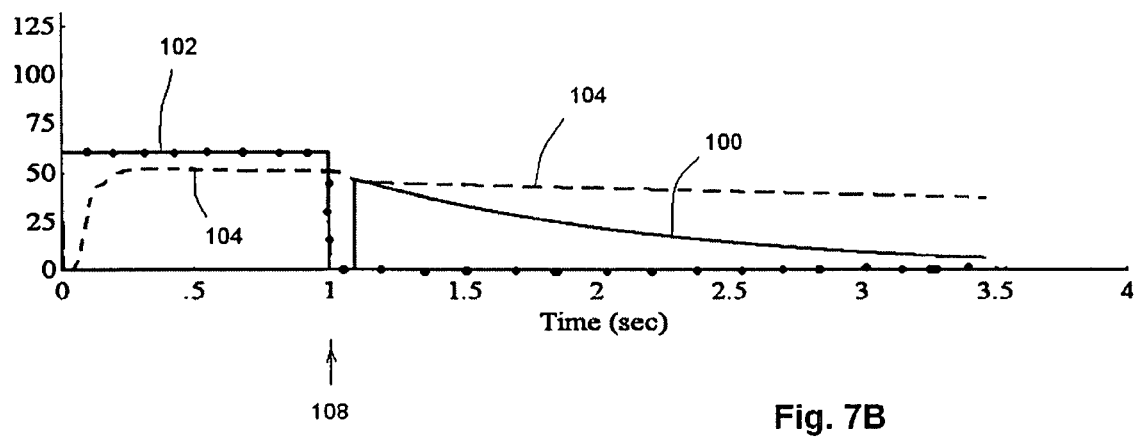

FIGS. 7A and 7B are graphs illustrating the occlusion detecting technique of this embodiment. Waveform 100 represents the occlusion threshold criterion $P_{occl}$ as determined above. Waveform 102 is a state signal indicating the respiratory state of the patient. A high value corresponds to the inspiratory state an a low value corresponds to an expiratory state. Waveform 104 corresponds to $P_{exh\_50}$. The start of the exhalation is indicated at 108. It can be appreciated that $P_{occl}$ is a decaying exponential function and begins approximately 100 ms after the exhalation begins.

FIG. 7A illustrates a situation in where there is no airway occlusion, and FIG. 7B illustrates a situation in which the airway is occluded. In FIG. 7B, it can be appreciated that $P_{exh\_50}$ 104 remains above (greater than) $P_{occl}$ for most of the duration of the exhalation. The opposite occurs in FIG. 7A.

In a third exemplary embodiment, an airway occlusion is declared based on the maximum flow that is expected to leave the patient while his/hers airway is obstructed. During the exhalation phase of any breath (i.e. while the ventilator is providing VCV, PCV, PSV or CPAP therapy), and while in the speaking mode, the pressure at the wye is used to estimate the maximum flow that is expected to leave the patient while his/hers airway is obstructed. In this embodiment, a critical volume is defined as the volume created by the integration of the maximum flow expected to leave the patient while his/hers airway is obstructed. The critical volume is calculated as follows:

$$\text{Critical\_Volume} = \sum_{n=1}^{m} Q occl(n) \quad (3)$$

where:
$Q_{occl}(n)=1\text{E}-05*|\text{Pexh}(n)|^3-0.0019*|\text{Pexh}(n)|^2+0.1581*|\text{Pexh}(n)|+0.2424$,
$Q_{occl}(n)$ is given in lpm,
n=control cycle number,
m=number of exhalation control cycles, and
If Pexh(n) is negative then $Q_{occl}(n)=-Q_{occl}1(n)$.

To detect an airway occlusion, the estimated flow is integrated and compared to the volume delivered to the patient tubing system on the next inhalation. If the volume delivered on the next inhalation (Vdel_next_breath) to the patient tubing system is less on each of two contiguous breaths, an occlusion of the airway is declared. Vdel_next_breath is defined as follows:

$$\text{Vdel\_next\_breath} = \sum_{k=1}^{j} Qtot(k) - \sum_{k=1}^{j} Qoccl(k) \quad (4)$$

where:
$Q_{tot}(k)=Q_{air}(k)+Q_{O2}(k)$=Flow delivered by the ventilator for the kth control interval,
$Q_{occl}(k)$ has been defined above,
k=control cycle number, and
j=number of inhalation control cycles.

As explained before, when an airway occlusion is detected, the exhalation valve is opened until the next inhalation is initiated. Ventilation will resume with the exhalation valve closing during inhalations and opening during exhalation phases until the occlusion condition is manually reset by the user. Once the condition is reset, the exhalation valve operation returns to be closed, in both inhalation and exhalation phases, starting at the beginning of the next breath's inhalation. This occlusion detection technique is particularly useful in situations where there are significant fluctuations in the pressure Py, making the other occlusion detection techniques difficult to implement.

A fourth exemplary embodiment for detecting an airway occlusion is used when the ventilator is operating in a CPAP mode, i.e., the ventilator is not providing mandatory breaths. During the exhalation phase while in CPAP mode and while the speaking mode is implemented, the exhalation valve is opened when the time elapsed since the beginning of the breath is equal to the lesser of an apnea interval minus inhalation time and minus 2 seconds or 8 seconds of exhalation time.

The exhaled volume will then be computed by integrating the exhalation flow (as measured by the exhalation flow sensor). A comparison of the exhaled volume (Exhaled_Volume) and the volume delivered by the ventilator during the previous inhalation phase, compensated for the critical volume (Inhaled_Volume−Critical_Volume), is carried out at the beginning of the next inhalation phase. If Exhaled_Volume>0.5*(Inhaled_Volume−Critical_Volume) then an airway occlusion is declared.
Where:

$$\text{Exhaled\_Volume} = \sum_{n=1}^{m} Qexh(n) - Pexh(m) \cdot Ctube \quad (5)$$

$$\text{Inhaled\_Volume} = \sum_{k=1}^{j} Qtot(k) - Pexh(j) \cdot Ctube \quad (6)$$

Ctube=Patient-Tubing circuit compliance. Given in ml/cmH2O
Pexh(j)=Tubing circuit pressure measurement, made by the exhalation pressure sensor, on the last control interval cycle for the previous inhalation phase.
Pexh(m)=Tubing circuit pressure measurement, made by the exhalation pressure sensor, on the last control interval cycle for the current exhalation phase.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of operating a ventilator assembly having inhalation and exhalation passages communicating with one another, a controller, inhalation and exhalation monitors, and a respiration assembly including inhalation and exhalation valves respectively communicating with the inhalation and exhalation passages, the respiration assembly performing repetitive respiratory cycles, each cycle including inhalation and exhalation phases, the method comprising acts of:
   the controller repetitively operating the respiration assembly through the respiratory cycles by controlling the inhalation and exhalation valves so that
   during the inhalation phase the inhalation valve is relatively open for the passage of gas therethrough into the inhalation passage to a patient and the exhalation valve is relatively closed, thus the gas in the inhalation passage flows through an endotracheal tube into the patient's airway and lungs below the patient's vocal cords, and
   during the exhalation phase the controller providing talking and non-talking modes, in the talking mode the inhalation valve is maintained relatively closed and the exhalation valve is maintained relatively closed to enable the patient to exhale the gases in the patient's airway and lungs past the patient's vocal cords and out of the patient's mouth, thereby facilitating the patient's ability to speak, and in the non-talking mode the inhalation valve is maintained relatively closed restricting inhalation gas from the patient and the atmosphere and the exhalation valve is maintained relatively open;

one or more of the inhalation and exhalation monitors monitoring a pressure within at least one of the inhalation and exhalation passages during the exhalation phase; and the controller determining whether a circuit disconnect or an occlusion exists based on the pressure monitoring, wherein the endotracheal tube has a check valve so that the gas exhaled by the patient during each exhalation phase is prevented from communicating with the passages.

2. The method of claim 1, wherein determining whether the circuit disconnect exists includes acts of:

determining a peak pressure during the exhalation phase; and comparing the peak pressure to a first threshold.

3. The method of claim 2, wherein determining whether the circuit disconnect exists further comprises acts of:

determining a minimum pressure during the exhalation phase;

determining a delta pressure as a difference between the minimum pressure and the peak pressure; and comparing the delta pressure to a second threshold.

4. The method of claim 1, wherein determining whether an occlusion exists further comprises acts of:

comparing the pressure to a threshold; and monitoring an amount of time that the pressure exceeds the threshold.

5. The method of claim 1, wherein determining comprises acts of:

determining occlusion criteria, wherein the occlusion criteria is a time varying function based on the pressure;

comparing the pressure to the occlusion criteria.

6. The method of claim 1, wherein determining whether an occlusion exists further comprises acts of:

determining a critical volume of gas expected to leave the patient in the presence of an obstruction; and comparing a volume of gas delivered from the ventilator assembly to the critical volume.

7. The method of claim 1, wherein determining whether an occlusion exists further comprises acts of:

determining an exhaled volume delivered by the ventilator assembly;

determining an inhaled volume delivered by the ventilator assembly;

comparing the exhaled volume to the inhaled volume or a volume determined based on the inhaled volume.

8. The method of claim 1, wherein during the exhalation phase, the inhalation valve or the exhalation valve is controlled to regulate pressure in a conduit providing communication between the inhalation and exhalation passages to facilitate the patient's ability to speak.

9. The method of claim 1, wherein the pressure in a conduit providing communication between the inhalation and exhalation passages is regulated by controlling opening and closing of at least one of the valves so as to provide a desired pressure in the conduit to facilitate the patient's ability to speak.

10. A patient ventilator assembly comprising:

an endotracheal tube having an exterior open end;

a conduit connected to the exterior open end of the endotracheal tube, the conduit includes inhalation and exhalation passages communicating with one another;

a respiration assembly including inhalation and exhalation valves respectively communicating with the inhalation and exhalation passages;

a pressure sensor adapted to monitor a pressure within at least one of the passages during the exhalation phase; and a controller for repetitively controlling the inhalation valve and the exhalation valve to provide respiratory cycles, each respiratory cycle including an inhalation phase and an exhalation phase, during the inhalation phase the inhalation valve is relatively open for the passage of gas therethrough into an inhalation passage to a patient and the exhalation valve is relatively closed, thus a flow of gas is allowed to pass through the inhalation passage and the endotracheal tube into the patient's airway and lungs below the patient's vocal cords, during the exhalation phase the controller providing two modes, in a first mode the inhalation valve is maintained relatively closed restricting inhalation gas from the patient and the atmosphere, and the exhalation valve is maintained relatively open allowing the gas in the patient's airway and lungs after the preceding inhalation phase to pass through the relatively open exhalation valve and through an outlet of the ventilator assembly, and a second mode wherein the inhalation valve is maintained relatively closed and the exhalation valve is maintained relatively closed so that the patient causes the gas in the patient's airway and lungs after the preceding inhalation phase to flow past the patient's vocal cords and out of the patient's mouth, thus facilitating the patient's ability to talk, and wherein the controller is adapted to determine whether a circuit disconnect or an occlusion exists based on the monitored pressure and wherein the endotracheal tube has a check valve so that the gas exhaled by the patient during each exhalation phase is prevented from communicating with the passages.

11. The patient ventilator assembly of claim 10, wherein the controller comprises an exhalation controller module that controls the exhalation valve and an inhalation controller module that controls the inhalation valve.

12. The patient ventilator assembly of claim 10, wherein the controller comprises a first algorithm for controlling the inhalation valve, a second algorithm for controlling the exhalation valve, and a third for determining whether the circuit disconnect or the occlusion exists.

13. The patient ventilator assembly of claim 10, wherein the exhalation valve is controlled by the controller to be closed sufficiently during the inhalation phase to enable a desired pressure to build within the conduit.

14. The patient ventilator assembly of claim 10, wherein the exhalation valve is controlled by the controller to be closed sufficiently during the exhalation phase to maintain a desired pressure in the conduit.

15. The patient ventilator assembly of claim 10, wherein the controller determines whether the circuit disconnect exists by determining a peak pressure during the exhalation phase, and comparing the peak pressure to a first threshold.

16. The patient ventilator assembly of claim 15, wherein the controller determines whether the circuit disconnect exists by:

determining a minimum pressure during the exhalation phase;

determining a delta pressure as a difference between the minimum pressure and the peak pressure; and comparing the delta pressure to a second threshold.

17. The patient ventilator assembly of claim 10, wherein the controller determines whether an occlusion exists by comparing the pressure to a threshold, and monitoring an amount of time that the pressure exceeds the threshold.

18. The patient ventilator assembly of claim 10, wherein the controller determines whether an occlusion exists by determining an occlusion criteria, wherein the occlusion criteria is a time varying function based on the pressure, and comparing the pressure to the occlusion criteria.

19. The patient ventilator assembly of claim 10, wherein the controller determines whether an occlusion exists by determining a critical volume of gas expected to leave the patient in the presence of an obstruction, and comparing a volume of gas delivered from the ventilator assembly to the critical volume.

20. The patient ventilator assembly of claim 10, wherein the controller determines whether an occlusion exists by determining an exhaled volume delivered by the ventilator assembly, determining an inhaled volume delivered by the ventilator assembly, and comparing the exhaled volume to the inhaled volume or a volume determined based on the inhaled volume.

21. A patient ventilating apparatus comprising:
an endotracheal tube constructed and arranged to be installed into a patient's trachea below the patient's vocal cords so that an exterior open end thereof is exterior of the patient and an interior open end thereof communicates with the patient's airway and lungs;
a conduit connected with the exterior open end of the endotracheal tube and providing inhalation and exhalation passages communicating with one another;
a respiration assembly constructed and arranged to provide repetitive respiratory cycles, each cycle including
an inhalation phase during which an inhalation valve in the inhalation passage is maintained relatively open and an exhalation valve in the exhalation passage is maintained relatively closed, enabling a flow of gas to pass through the inhalation passage and the endotracheal tube into the patient's airway and lungs, and
an exhalation phase during which the inhalation valve is maintained relatively closed and the exhalation valve is maintained relatively closed, the exhalation phase having talking and non-talking modes;
a check valve operatively coupled to the endotracheal tube, in the talking mode the check valve maintains the exhalation valve relatively closed for enabling the patient to cause the gas in the patient's airway and lungs to pass through the patient's vocal cords and out of the patient's mouth, thus facilitating the patient's ability to speak, the check valve being operable to trap pressure within the patient's lungs at the end of the inhalation phase when both the inhalation and exhalation valves are relatively closed so as to allow pressure in the passages at the end of each inhalation phase to substantially equalize with the pressure within the patient's airway and lungs during the talking mode of the exhalation phase; and
a pressure monitor adapted to monitor a pressure in at least one of the inhalation and exhalation passages during the exhalation phase; and
a controller that controls operation of the inhalation valve and the exhalation valve, and determines whether a circuit disconnect or an occlusion exists based on the monitored pressure.

22. The patient ventilating apparatus of claim 21, wherein during the inhalation phase, the flow of gas is allowed to pass through the exhalation valve.

23. The patient ventilating apparatus of claim 21, wherein the controller determines whether the circuit disconnect exists by determining a peak pressure during the exhalation phase, and comparing the peak pressure to a first threshold.

24. The patient ventilating apparatus of claim 22, wherein the controller determines whether the circuit disconnect exists by:
determining a minimum pressure during the exhalation phase;
determining a delta pressure as a difference between the minimum pressure and the peak pressure; and
comparing the delta pressure to a second threshold.

25. The patient ventilating apparatus of claim 21, wherein the controller determines whether an occlusion exists by comparing the pressure to a threshold, and monitoring an amount of time that the pressure exceeds the threshold.

26. The patient ventilating apparatus of claim 21, wherein the controller determines whether an occlusion exists by determining an occlusion criteria, wherein the occlusion criteria is a time varying function based on the pressure, and comparing the pressure to the occlusion criteria.

27. The patient ventilating apparatus of claim 21, wherein the controller determines whether an occlusion exists by determining a critical volume of gas expected to leave the patient in the presence of an obstruction, and comparing a volume of gas delivered from the ventilator assembly to the critical volume.

28. The patient ventilating apparatus of claim 21, wherein the controller determines whether an occlusion exists by determining an exhaled volume delivered by the ventilator assembly, determining an inhaled volume delivered by the ventilator assembly, and comparing the exhaled volume to the inhaled volume or a volume determined based on the inhaled volume.

* * * * *